United States Patent
Brennan et al.

(10) Patent No.: US 8,997,672 B2
(45) Date of Patent: *Apr. 7, 2015

(54) SURFACE TOPOGRAPHIES FOR NON-TOXIC BIOADHESION CONTROL

(75) Inventors: Anthony B. Brennan, Gainesville, FL (US); Ronald Howard Baney, Gainesville, FL (US); Michelle Carman Turnage, Jacksonville, FL (US); Thomas G. Estes, Atlanta, GA (US); Adam W. Feinberg, Cambridge, MA (US); Leslie H. Wilson, Jacksonville, FL (US); James Frederick Schumacher, Cumming, GA (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 94 days.
This patent is subject to a terminal disclaimer.

(21) Appl. No.: 12/624,503

(22) Filed: Nov. 24, 2009

(65) Prior Publication Data
US 2010/0126404 A1 May 27, 2010

Related U.S. Application Data

(60) Division of application No. 11/567,103, filed on Oct. 5, 2006, now Pat. No. 7,650,848, which is a
(Continued)

(51) Int. Cl.
*B63B 59/04* (2006.01)
*B08B 17/02* (2006.01)
(Continued)

(52) U.S. Cl.
CPC ............... *B08B 17/06* (2013.01); *A61F 2/0077* (2013.01); *A61F 2002/0086* (2013.01);
(Continued)

(58) Field of Classification Search
CPC ........ B63B 1/36; B63B 59/04; Y02T 70/121; Y02T 70/123; B08B 17/06; B08B 17/065; B81C 1/00023; B81C 1/00031; B81C 1/00047; B81C 1/00055; B81C 1/00063; B81C 1/00071; A41D 31/0077; B64D 15/00; A61L 2/02; F05C 2253/12; A61F 2/0077; A61F 2/12; A61F 2/24; A61F 2002/0086; A61F 2002/009
USPC ........... 114/67 A, 222, 67 R; 405/216; 422/6; 428/141–145; 244/200, 200.1, 204, 244/204.1, 130; 424/400; 473/378–385; 623/23.5, 23.74
See application file for complete search history.

(56) References Cited

U.S. PATENT DOCUMENTS 3,243,850 A 4/1966 Zieg
3,351,441 A 11/1967 Gewiss et al.
(Continued)

FOREIGN PATENT DOCUMENTS

CA 2368204 10/2000
DE 3801139 C1 3/1989
(Continued)

OTHER PUBLICATIONS

Machine translation of JP 05-010309 A.*
(Continued)

*Primary Examiner* — Ajay Vasudeva
(74) *Attorney, Agent, or Firm* — Cantor Colburn LLP

(57) ABSTRACT

An article has a surface topography for resisting bioadhesion of organisms and includes a base article having a surface. A composition of the surface includes a polymer. The surface has a topography comprising a pattern defined by a plurality of spaced apart features attached to or projected into the base article. The plurality of features each have at least one microscale dimension and at least one neighboring feature having a substantially different geometry. An average feature spacing between adjacent ones of the features is between 10 μm and 100 μm in at least a portion of the surface. The surface topography can be numerically represented using at least one sinusoidal function. In one embodiment, the surface can comprise a coating layer disposed on the base article.

17 Claims, 13 Drawing Sheets

Related U.S. Application Data continuation-in-part of application No. 11/202,532, filed on Aug. 12, 2005, now Pat. No. 7,143,709, which is a continuation-in-part of application No. 10/780,424, filed on Feb. 17, 2004, now Pat. No. 7,117,807.

(51) Int. Cl.
| | |
|---|---|
| B08B 17/06 | (2006.01) |
| A61F 2/02 | (2006.01) |
| A61L 27/00 | (2006.01) |
| B64D 15/00 | (2006.01) |
| B81C 1/00 | (2006.01) |
| A61F 2/00 | (2006.01) |
| A61F 2/12 | (2006.01) |
| B63B 1/36 | (2006.01) |

(52) U.S. Cl.
CPC ............ *A61F 2002/009* (2013.01); *A61F 2/12* (2013.01); *B08B 17/065* (2013.01); *B63B 1/36* (2013.01); *B63B 59/04* (2013.01); *B64D 15/00* (2013.01); *B81C 1/00206* (2013.01); *F05C 2253/12* (2013.01); *Y02T 70/121* (2013.01); *Y02T 70/123* (2013.01)

(56) References Cited

U.S. PATENT DOCUMENTS

| | | | | |
|---|---|---|---|---|
| 3,354,022 | A * | 11/1967 | Johnson, Jr. et al. | 428/167 |
| 3,795,471 | A | 3/1974 | Milani | |
| 3,935,485 | A | 1/1976 | Yoshida et al. | |
| 3,971,084 | A | 7/1976 | Spier | |
| 3,992,162 | A | 11/1976 | Gewiss | |
| 3,996,323 | A | 12/1976 | Hegler et al. | |
| 4,101,625 | A | 7/1978 | Haley | |
| 4,283,461 | A | 8/1981 | Wooden et al. | |
| 4,284,689 | A * | 8/1981 | Craighead et al. | 428/620 |
| 4,297,394 | A | 10/1981 | Wooden et al. | |
| 4,640,859 | A | 2/1987 | Hansen et al. | |
| 4,865,603 | A | 9/1989 | Noiles | |
| 5,008,140 | A | 4/1991 | Schmertz | |
| 5,028,474 | A | 7/1991 | Czaplicki | |
| 5,328,200 | A * | 7/1994 | Pelizzari | 280/609 |
| 5,344,691 | A | 9/1994 | Hanschen et al. | |
| 5,403,680 | A | 4/1995 | Otagawa et al. | |
| 5,645,764 | A | 7/1997 | Angelopoulos et al. | |
| 5,650,214 | A | 7/1997 | Anderson et al. | |
| 5,842,937 | A * | 12/1998 | Dalton et al. | 473/384 |
| 5,971,326 | A | 10/1999 | Bechert | |
| 5,976,284 | A | 11/1999 | Calvert et al. | |
| 6,010,442 | A * | 1/2000 | Lemons et al. | 473/384 |
| 6,075,585 | A | 6/2000 | Minne et al. | |
| D430,734 | S | 9/2000 | Bredendick et al. | |
| D436,738 | S | 1/2001 | Bredendick et al. | |
| D440,051 | S | 4/2001 | Bredendick et al. | |
| 6,231,463 | B1 * | 5/2001 | Tavares et al. | 473/378 |
| D443,766 | S | 6/2001 | Bredendick et al. | |
| 6,394,652 | B2 | 5/2002 | Meyer et al. | |
| D459,897 | S | 7/2002 | Bredendick et al. | |
| 6,458,447 | B1 | 10/2002 | Cabell et al. | |
| 6,569,038 | B2 * | 5/2003 | Sullivan | 473/383 |
| 6,616,882 | B1 | 9/2003 | Lidgett | |
| 6,660,363 | B1 * | 12/2003 | Barthlott | 428/141 |
| 6,686,026 | B2 | 2/2004 | Spiewak et al. | |
| 6,911,243 | B2 | 6/2005 | Sher et al. | |
| 6,946,170 | B2 | 9/2005 | Gerber et al. | |
| D518,648 | S | 4/2006 | Broering et al. | |
| 7,117,536 | B2 | 10/2006 | Burnett et al. | |
| 7,117,807 | B2 * | 10/2006 | Bohn et al. | 114/222 |
| 7,143,709 | B2 * | 12/2006 | Brennan et al. | 114/222 |
| 7,303,491 | B2 * | 12/2007 | Nardacci et al. | 473/378 |
| 7,650,848 | B2 * | 1/2010 | Brennan et al. | 114/222 |
| 7,691,464 | B2 | 4/2010 | Gerber et al. | |
| 2002/0150724 | A1 | 10/2002 | Nun et al. | |
| 2003/0228445 | A1 | 12/2003 | Vaughn et al. | |
| 2004/0086674 | A1 | 5/2004 | Holman | |
| 2004/0191538 | A1 | 9/2004 | Huang | |
| 2005/0003146 | A1 * | 1/2005 | Spath | 428/105 |
| 2005/0008828 | A1 | 1/2005 | Libera et al. | |
| 2005/0119723 | A1 | 6/2005 | Peacock | |
| 2005/0119758 | A1 | 6/2005 | Alexander et al. | |
| 2005/0136217 | A1 * | 6/2005 | Barthlott et al. | 428/141 |
| 2005/0178286 | A1 | 8/2005 | Bohn, Jr. et al. | |
| 2006/0219143 | A1 | 10/2006 | Brennan et al. | |
| 2007/0098957 | A1 * | 5/2007 | Barthlott et al. | 428/141 |
| 2007/0227428 | A1 | 10/2007 | Brennan et al. | |
| 2008/0202370 | A1 | 8/2008 | Muraoka | |
| 2010/0033818 | A1 | 2/2010 | Petcavich et al. | |
| 2010/0119755 | A1 | 5/2010 | Chung et al. | |
| 2010/0226943 | A1 | 9/2010 | Brennan et al. | |

FOREIGN PATENT DOCUMENTS

| | | | |
|---|---|---|---|
| DE | 19613304 | A1 * | 10/1997 |
| DE | 19840303 | A1 * | 3/2000 |
| EP | 0015312 | A1 | 9/1980 |
| EP | 1469198 | A1 * | 10/2004 |
| GB | 722591 | | 1/1955 |
| JP | 05010309 | A * | 1/1993 |
| JP | 2001207123 | A * | 7/2001 |
| WO | WO9325171 | | 12/1993 |
| WO | WO9604123 | | 2/1996 |
| WO | WO0058410 | | 10/2000 |
| WO | WO2006026933 | | 3/2006 |
| WO | WO2008070625 | | 6/2008 |

OTHER PUBLICATIONS

Fractals Are SMART: Fractal Pack 1 Educators' Guide. Downloaded from FractalFoundation.org. Copyright 2009.*

A. Tuteja, et al. "Designing Superoleophobic Surfaces" Science (Dec. 7, 2007) pp. 1618-1622, ScienceMag.org.

B. He, et al. "Multiple Equilibrium Droplet Shapes and Design Criterion for Rough Hydrophobic Surfaces", Langmuir (2003) pp. 4999-5003, vol. 19; American Chemical Society.

D. Quere "Wetting and Roughness" Annu. Rev. Mater. Res. (2008) pp. 71-99 vol. 38, Annual Reviews.

D.M. Spori, et al. "Beyond the Lotus Effect: Roughness Influences on Wetting Over a Wide Surface-Energy Range" Langmuir (2008) pp. 5411-5417, vol. 24, American Chemical Society.

D.W. Bechert, et al. "Fluid Mechanics of Biological Surfaces and their Technological Application", Naturwissenschaften (2000) pp. 157-171; vol. 87; Springer-Verlag, Germany.

E. Martines, et al. "Superhydrophobicity and Superhydrophilicity of Regular Nanopatterns" Nano Letters (2005) pp. 2097-2103, vol. 5, No. 10, American Chemical Society.

G.McHale, et al. "Analysis of Droplet Evaporation on a Superhydrophobic Surface" Langmuir (2005) pp. 11053-11060, vol. 21, American Chemical Society.

H.C. Flemming, "Biofouling in Water Systems—Cases, Causes and Countermeasures", Appl. Microbiol Biotechnol (2002), pp. 629-640, vol. 59; Springer-Verlag, Germany.

J. Bico, et al. "Wetting of Textured Surfaces", Colliods and Surfaces (2002) pp. 41-46, vol. 206; Elsevier Science B.V.

J. Bico, et al. "Pearl Drops" Europhysics Letters (Jul. 15, 1999) pp. 220-226; vol. 47 (2); EDP Sciences.

J. Genzer, et al. "Recent Developments in Superhydrophobic Surfaces and their Relevance to Marine Fouling: A Review" Biofouling (2006) pp. 1-22, Taylor & Francis.

J.M. Hills, et al. "Settlement of Barnacle Larvae is Governed by Euclidean and not Fractal Surface Characteristics" Functional Ecology (1999), pp. 868-875, vol. 13, British Ecological Society.

L.D. Chambers, et al. "Modern Approaches to Marine Antifouling Coatings" Surface and Coatings Technology (2006) pp. 3642-3652, vol. 201, Elsevier B.V.

M.E. Abdelsalam, et al. "Wetting of Regularly Structured Gold Surfaces" Langmuir (2005) pp. 1753-1757, vol. 21, American Chemical Society.

(56) References Cited

OTHER PUBLICATIONS

M.E. Callow, et al. "Microtopographic Cues for Settlement of Zoospores of the Green Fouling Alga Enteromorpha", Biofouling (2002) pp. 237-245; vol. 18 (3); Taylor & Francis, UK.
R. Furstner, et al. "Wetting and Self-Cleaning Properties of Artificial Superhydrophobic Surfaces", Langmuir (2005), pp. 956-961, vol. 21; American Chemical Society.
W.R. Hansen, et al. "Evidence for Self-Cleaning in Gecko Setae" Evolution (Jan. 11, 2005) pp. 385-389, vol. 102 vol. 2; PNAS.
Y. Chen, et al. "Anisotropy in the Wetting of Rough Surfaces", Journal of Colloid and Interface Sciences (2005), pp. 458-464, vol. 281; Elsevier Inc.
Z. Burton, et al. "Hydrophobicity, Adhesion, and Friction Properties of Nanopatterned Polymers and Scale Dependence for Micro- and Nanoelectromechanical Systems" Nano Letters (2005) pp. 1607-1613, vol. 5 No. 8, American Chemical Society.
Patent Abstract of Japan; Publication No. 10-123693; May 15, 1998 (1 page).
Patent Abstracts of Japan; 62-046232 dated Feb. 28, 1987—(1 page).
Callow et al. "Primary adhesion of enteromorphia (chlorophyta, ulvales) propagules: quantitative settlement studies and video microscopy", J. Phycol., 1997, vol. 33 pp. 938-947.
Cassie et al. "Wettability of porous surfaces", Trans. Faraday Society, 1944, vol. 40, pp. 546-551.
European Search Report for Appl. 12172148.4 dated Nov. 23, 2012, 13 pages.
Horiuchi et al. "Optical lithography onto inside surfaces of small-diameter pipes" Microelectronic Engineering 85 (2008) 1043-1046—Elsevier.
International Search Report dated Jun. 13, 2006 for Application No. PCT/US05/04972—4 pages.
International Search Report dated May 22, 2008 for Application No. PCT/US07/86289—10 pages.
Quere "Rough ideas on wetting", Physica A, 2002 vol. 313, pp. 32-46.
Search Report dated Jun. 25, 2010 for Application No. PCT/US09/064160—8 pages.
Wenzel "Resistance of solid surfaces to wetting by water", Industrial and Engineering Chemistry, 1936, vol. 28, No. 8, pp. 988-994.
Written Opinion dated Jun. 13, 2006 for Application No. PCT/US05/04972—6 pages.
Written Opinion dated May 22, 2008 for Application No. PCT/US07/86289—6 pages.
Written Opinion dated Jun. 25, 2010 for Application No. PCT/US09/064160—6 pages.
Xia et al. "Soft Lithography", Annu. Rev. Mater. Sci., 1998, vol. 28, pp. 153-184.

\* cited by examiner

|  | Depth (um) | Spacing (um) | Width (um) | Roughness Factor |
|---|---|---|---|---|
| Riblet | 5 | 2 | 2 | 5.0 |
| | 8 | 2 | 2 | 7.3 |
| | 10 | 2 | 2 | 8.9 |
| Star/Clover | 5 | 2 | 4 | 4.5 |
| | 8 | 2 | 4 | 6.6 |
| | 10 | 2 | 4 | 8.0 |
| | 5 | 2 | 2,4 | 3.6 |
| | 8 | 2 | 2,4 | 5.2 |
| | 10 | 2 | 2,4 | 6.2 |
| Gradient | 5 | 1,2,3,4 | 2 | 2.8 |
| | 8 | 1,2,3,4 | 2 | 3.8 |
| | 10 | 1,2,3,4 | 2 | 4.5 |
| Triangle/Circle | 5 | 1 | 1,5 | 7.5 |
| | 5 | 2 | 2,10 | 4.2 |
| | 5 | 3 | 3,15 | 3.2 |
| | 8 | 1 | 1,5 | 11.3 |
| | 8 | 2 | 2,10 | 6.2 |
| | 8 | 3 | 3,15 | 4.4 |
| | 10 | 1 | 1,5 | 13.9 |
| | 10 | 2 | 2,10 | 7.5 |
| | 10 | 3 | 3,15 | 5.3 |

100 μm

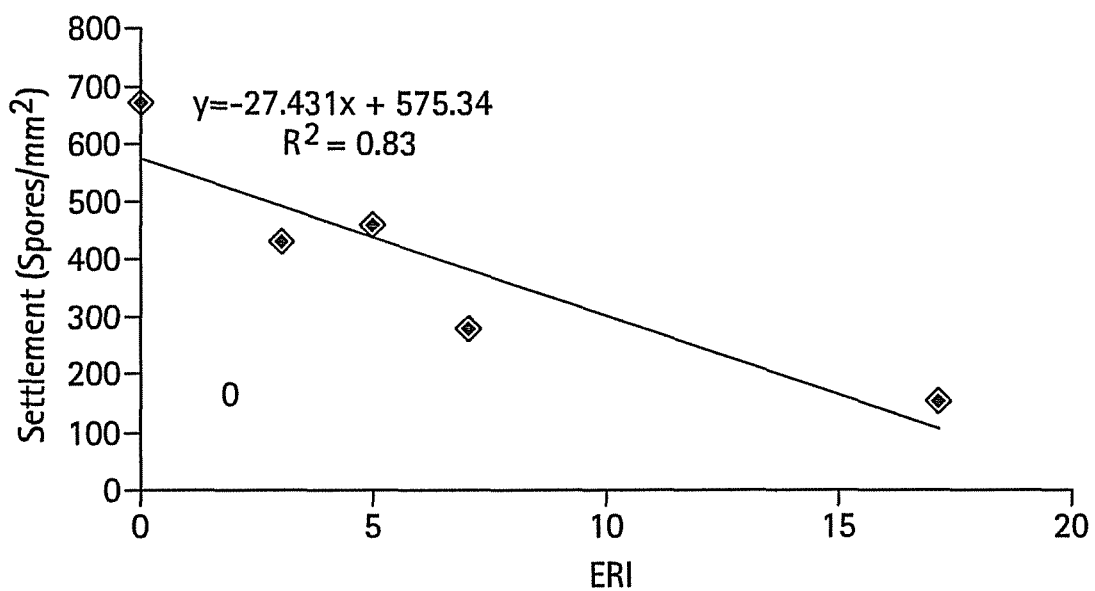

SURFACE TOPOGRAPHIES FOR NON-TOXIC BIOADHESION CONTROL

CROSS-REFERENCE TO RELATED APPLICATIONS

This application is a divisional application of U.S. patent application Ser. No. 11/567,103 filed on Dec. 5, 2006, now U.S. Pat. No. 7,650,848, which is a continuation-in-part (CIP) application of U.S. patent application Ser. No. 11/202,532 entitled "SURFACE TOPOGRAPHY FOR NON-TOXIC BIOADHESION CONTROL" which was filed on Aug. 12, 2005, now U.S. Pat. No. 7,143,709, which a CIP of U.S. patent application Ser. No. 10/780,424 entitled "DYNAMICALLY MODIFIABLE POLYMER COATINGS AND DEVICES" which was filed on Feb. 17, 2004, now U.S. Pat. No. 7,117,807, both being incorporated by reference in their entireties into the present application.

FIELD OF THE INVENTION

The invention relates to articles and related devices and systems having surface topography and/or surface elastic properties for providing non-toxic bioadhesion control.

BACKGROUND

Biofouling is the unwanted accumulation of organic and inorganic matter of biological origin on surfaces. For example, in the marine environment biofouling is the result of marine organisms settling, attaching, and growing on submerged marine surfaces. The biofouling process is initiated within minutes of a surface being submerged in a marine environment by the absorption of dissolved organic materials which result in the formation of a conditioning film. Once the conditioning film is deposited, bacteria (e.g. unicellular algae) colonize the surface within hours of submersion. The resulting biofilm produced from the colonization of the bacteria is referred to as microfouling or slime and can reach thicknesses on the order of 500 μm.

Biofouling is estimated to cost the U.S. Navy alone over $1 billion per year by increasing the hydrodynamic drag of naval vessels. This in turn decreases the range, speed, and maneuverability of naval vessels and increases the fuel consumption by up to 30-40%. Thus, biofouling weakens the national defense. Moreover, biofouling is also a major economical burden on commercial shipping, recreational craft, as well as civil structures, bridges, and power generating facilities.

Any substrate in regular contact with water is likely to become fouled. No surface has been found that is completely resistant to fouling. Due to the vast variety of marine organisms that form biofilms, the development of a single surface coating with fixed surface properties for the prevention biofilm formation for all relevant marine organisms is a difficult if not impossible task.

Anti-fouling and foul-release coatings are two main approaches currently used for combating biofilm formation. Anti-fouling coatings prevent or deter the settling of biofouling organisms on a surface by the use of leached biocides, typically cuprous oxide or tributyltin, into the water. The biocides are either tethered to the coated surface or are released from the surface into the surrounding environment. Use of these types of coatings has caused damage to the marine ecosystem, especially in shallow bays and harbors, where the biocides can accumulate. As such, the use of tributyltin has been banned in many parts of the world. These products are effective for only approximately 2 to 5 years.

Foul release coatings present a hydrophobic, low surface energy, and resulting slippery surface that minimizes the adhesion of the biofouling organisms. The most commonly used and highly successful of these is a nontoxic silicone-based paint. The silicone-based coating requires several layers to make it effective, and therefore it can be quite costly. Effectiveness lasts up to 5 years at which time recoating may become necessary. These products are considered to be more environmentally sound as compared to anti-fouling coatings because they do not leach toxins. However, they are subject to abrasion, and therefore their use is limited to areas that are not susceptible to damage caused by ice or debris.

Biofouling is similarly a problem for surfaces used in biomedical applications. The accumulations of bacteria, i.e. a biofilm, on implanted devices such as orthopedic prosthesis present a significant risk of infection leading to complications as severe as death. In cosmetic implants, devices such as breast implants are fouled with fibroblasts and acellular extracellular matrix resulting in a hard fibrous capsule and subsequent implant rupture. Blood contacting surfaces such as artificial heart valves and artificial vascular grafts are fouled by proteins such as fibrinogen that initiate the coagulation cascade leading in part to heart attack and stroke. The accumulated affect of bio fouling on chronic and acute disease states, its contribution to morbidity and its massive medical expenses places biofouling as one of the major issues facing modern medicine.

SUMMARY OF THE INVENTION

An article has a surface topography for resisting bioadhesion of organisms and includes a base article having a surface. The chemical composition of the surface comprises a polymer. The surface has a topography comprising a pattern defined by a plurality of spaced apart features attached to or projected into the base article. The plurality of features each have at least one microscale dimension and at least one neighboring feature having a substantially different geometry. An average spacing between adjacent ones of the features is between 10 μm and 100 μm in at least a portion of the surface.

Surface topographies according to the invention resist bioadhesion as compared to the base article. As used herein, a surface that provides a surface topography according to the invention can be applied to a surface as either a printed patterned, adhesive coating containing the topography, or applied directly to the surface of the device through micromolding. In the case of micromolding, the surface topography will be monolithically integrated with the underlying article.

The feature spacing distance as used herein refers to the distance between adjacent features. Moreover, as used herein, "microscale features" includes micron size or smaller features, thus including microscale and nanoscale.

In one embodiment of the invention referred to as a hierarchical architecture, at least one multi-element plateau layer is disposed on a portion of the surface. A spacing distance between elements of the plateau layer provides a second feature spacing being substantially different as compared to the first feature spacing. The hierarchical architecture can simultaneously repel organisms having substantial different sizes, such as spores and barnacles. In one embodiment the surface is monolithically integrated with the base article, wherein a composition of the base article is the same as the composition of the surface. In another embodiment, the surface comprises a coating layer disposed on the base article. In this coating embodiment, the composition of the coating layer is different as compared to a composition of the base article, and the polymer can comprise a non-electrically conductive polymer, such as selected from elastomers, rubbers, polyurethanes and polysulfones.

The topography can provide an average roughness factor (R) of from 4 to 50 and an elastic modulus of between 10 kPa and 10 MPa. In another embodiment, the topography is numerically representable using at least one sinusoidal function, such as two different sinusoidal waves. An example of a two different sinusoidal wave topography comprises a Sharklet topography. In another embodiment, the plurality of spaced apart features can have a substantially planar top surface. In a preferred embodiment for controlling barnacles, the first feature spacing can be between 15 and 60 μm.

In the multi-element plateau layer disposed on a portion of surface embodiment, wherein a spacing distance between elements of the plateau layer provide a second feature spacing being substantially different as compared to the first feature spacing, the surface can comprise a coating layer disposed on the base article. The elastic modulus of the coating layer can be between 10 kPa and 10 MPa.

The base article can comprise a roofing material. In another embodiment, the base article comprises a water pipe, wherein the surface is provided on an inner surface of a water inlet pipe. In this embodiment, the inlet pipe can be within a power plant in another embodiment, the base article comprises an implantable device or material, such as a breast implant, a catheter or a heart valve.

In another embodiment of the invention, an article has a surface topography for resisting bioadhesion of organisms, comprising a base article having a surface. The composition of the surface comprises a polymer, the surface having a topography comprising a pattern defined by a plurality of spaced apart features attached to or projected into the base article. The plurality of features each have at least one microscale dimension and at least one neighboring feature having a substantially different geometry, wherein an average first feature spacing between adjacent ones of the features is microscale and topography is numerically representable using at least one sinusoidal function. The surface can comprise a coating layer disposed on the base article. In a first embodiment the first feature spacing is between 0.5 and 5 μm in at least a portion of the surface, while in a second embodiment the first feature spacing is between 15 and 60 μm in at least a portion of the surface. The at least one sinusoidal function can comprise two different sinusoidal waves, such as a Sharklet topography. The article can further comprise at least one multi-element plateau layer disposed on a portion of the surface, wherein a spacing distance between elements of the plateau layer provide a second feature spacing being substantially different as compared to the first feature spacing.

BRIEF DESCRIPTION OF THE DRAWINGS

A fuller understanding of the present invention and the features and benefits thereof will be obtained upon review of the following detailed description together with the accompanying drawings, in which:

FIG. 3 provides a table of exemplary feature depths, feature spacings, feature widths and the resulting roughness factor (R) based on the patterns shown in FIGS. 2(a)-(d).

FIG. 6(c) shows the resulting layout between two elements by setting the spacing to 3 microns.

FIG. 7(b) shows the result of applying sinusoidal waves to define periodic repeat definitions, while

FIG. 8(b) is a scanned light micrograph image showing algae spores on the surface of the control sample, while

FIG. 9 shows a correlation between Ulva Spore settlement density and the corresponding Engineered Roughness Index (ERI) for several topographical patterns according to the invention (shown in A-D above the correlation data).

DETAILED DESCRIPTION OF THE INVENTION

Figure 1A:
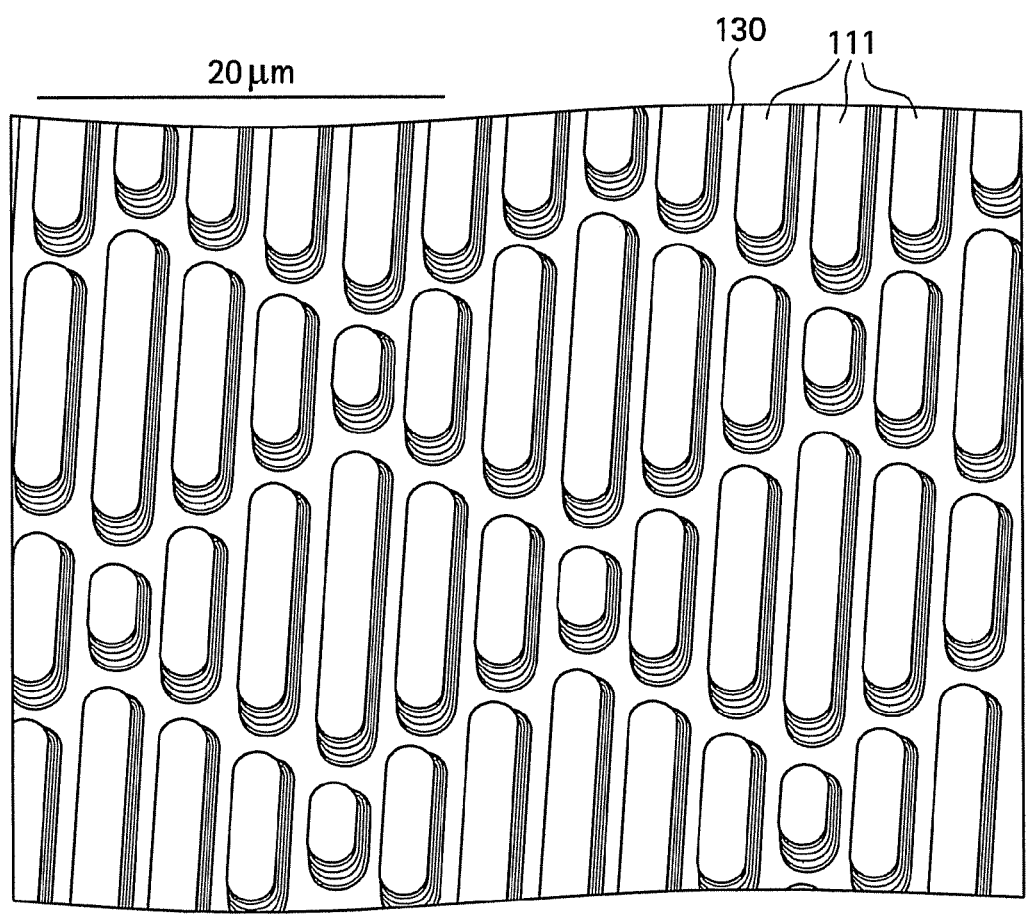
FIG. 1(a) is a scanned SEM image of an exemplary "Sharklet" anti-algae surface topography comprising a plurality of raised surface features which project out from the surface of a base article, according to an embodiment of the invention.

The present invention describes a variety of scalable surface topographies for modification of bio settlement and bioadhesion, such as bioadhesion of biofouling organisms, including, but not limited to, algae, bacteria and barnacles. As described in the Examples described below, it has been proven through experimental testing that surface topographies according to the invention provide a passive and non-toxic surface, which through selection of appropriate feature sizes and spacing, can significantly and generally dramatically reduce settlement and adhesion of the most common fouling marine algae known, as well as the settlement of barnacles.

Although not required to practice the present invention, Applicants not seeking to be bound by the mechanism believed to be operable to explain the efficacy of the present invention, provide the following. The efficacy of surfaces according to the invention is likely to be due to physically interfering with the settlement and adhesion of microorganisms, such as algae, bacteria and barnacles. Properly spaced features (such as "ribs") formed on or formed in the surface can be effective for organisms from small bacteria (<1 µm, such as 200 to 500 nm), to large tube worms (>200 µm, such as 200 to 500 µm), provided the feature spacing scales with the organism size. Specifically, bioadhesion is retarded when the specific width of closely packed, yet dissimilar features (e.g. ribs) in the pattern is too narrow to support settlement on top, yet the ribs are too closely packed to allow settlement in between. However, a feature spacing too small is believed to make the surface look flat to the settling organism, i.e. like the base surface, and thus ineffective. Accordingly, a feature spacing that scales with 25 to 75% of the settling organism's smallest physical dimension has been found to be generally effective to resist bioadhesion. Various different surface topographies can be combined into a hierarchical multi-level surface structure to provide a plurality of spacing dimensions to deter the settlement and adhesion of multiple organisms having multiple and wide ranging sizes simultaneously, such as algae, spores and barnacles.

Topographies according to the invention can generally be applied to a wide variety of surfaces for a wide variety of desired applications. Applications for inhibiting bioadhesion using the invention described in more detail below include base articles used in marine environments or biomedical or other applications which may be exposed to contamination by biological organisms, such as roofs on buildings, water inlet pipes in power plants, catheters, cosmetic implants, and heart valves. As described below, surfaces according to the invention can be formed on a variety of devices and over large areas, if required by the application.

Barnacles are known to be generally elliptically shaped have a nominal length of about 100 µm, and a nominal width of about 30 µm. Algae are also generally elliptically shaped and have a nominal length of about 7 µm, and a nominal width of about 2 µm, while spores are generally elliptically shaped have a nominal length of about 5 µm, and a nominal width of about 1.5 µm. Features according to the invention are generally raised surfaces (volumes) which emerge from a base level to provide a first feature spacing, or in the case of hierarchical multi-level surface structures according to the invention also include the a second feature spacing being the spacing distance between neighboring plateaus, which themselves preferably include raised features thereon or features projected into the base article.

As noted above, if the feature spacing is smaller than the smaller dimension of the organism or cell, it has been found that the growth is generally retarded, such between 0.25 and 0.75 of the smaller dimension of the cell or organism. A feature spacing of about ½ the smaller dimension of a given organism to be repelled has been found to be near optimum. For example, for an algae spore 2 to 5 µm in width, to retard adhesion, a feature spacing of from about 0.5 to 3.75 µm, preferably 0.75 to 2 µm is used. For example, to repel barnacles 20 to 50 µm in width, a feature spacing of between 5 and 200 µm, preferably 10 to 100 µm, has been found to be effective. For repelling both barnacles and spores, a hierarchical multi-level surface structure according to the invention can include a raised surfaces (volumes) which emerge from or are projected into a base level having a feature spacing of about 2 µm, and a plurality of striped plateau regions spaced 20 µm apart, the plateau regions also including raised surfaces (volumes) which emerge from or are projected into the plateau having a spacing of about 2 µm. One or more additional plateau regions can be used to repel additional organisms having other sizes. The additional plateau regions can be aligned (parallel) with the first plateau, or oriented at various other angles.

Although generally described for deterring bioadhesion, the invention can also be used to encourage bioadhesion, such as for bone growth. Feature dimensions of at least equal to about the size of the larger dimension of bioorganism or cells to be attached have been found to be effective for this purpose.

Although the surface is generally described herein as being an entirely polymeric, the coating can include non-polymeric elements that contribute to the viscoelastic and topographical properties. A "feature" as used herein is defined a volume (L, W and H) that projects out the base plane of the base material or an indented volume (L, W and H) which projects into the base material. The claimed architecture is not limited to any specific length. For example, two ridges of an infinite length parallel to one another would define a channel in between. In contrast, by reducing the overall lengths of the ridges one can form individual pillars. Although the surface is generally described as a coating which is generally a different material as compared to the base article, as noted above, the invention includes embodiments where the coating and base layer are formed from the same material, such as provided by a monolithic design, which can be obtainable by micromolding.

In the case of a surface coating, the coating can comprise a non-electrically conductive material, defined as having an electrical conductivity of less than $1 \times 10^{-6}$ S/cm at room temperature. The coating layer can comprise elastomers, rubbers, polyurethanes and polysulfones. The elastic modulus of the coating layer can be between 10 kPa and 10 MPa. In the case of 10 to 100 kPa materials, the coating can comprise hydrogels such as polyacrylic acid and thermo sensitive hydrogels such as poly isopropylacrylimide. The coating layer can be various thickness, such as 1 µm to 10 mm, preferably being between 100 µm to 1 mm.

Each of the features have at least one microscale dimension. In some embodiments, the top surface of the features are generally substantially planar.

Although feature spacing has been found to be the most important design parameter, feature dimensions can also be significant. In a preferred embodiment of the invention, each of the features include at least one neighboring feature having a "substantially different geometry". "Substantially different geometry" refers to at least one dimension being at least 10%, more preferably 50% and most preferably at least 100% larger than the smaller comparative dimension. The feature length or width is generally used to provide the substantial difference.

The feature spacing in a given pattern should generally be consistent. Studies by the present Inventors have indicated that small variations in micrometer scale spacing of the ribs that compose the surface features have demonstrated that less than 1 µm changes (10% or less than the nominal spacing) can significantly degrade coating performance. For example, the consistency of a 2 µm nominal spacing should be within ±0.2 µm for best retardation of *Ulva* settlement.

The composition of the patterned coating layer may also provide surface elastic properties which also can provide some bioadhesion control. In a preferred embodiment when bioadhesion is desired to be minimized, the coated surface distributes stress to several surrounding features when stress is applied to one of the features by an organism to be repelled from the surface.

The roughness factor (R) is a measure of surface roughness. R is defined herein as the ratio of actual surface area (Ract) to the geometric surface area (Rgeo); R=Ract/Rgeo. An example is provided for a 1 cm$^2$ piece of material. If the sample is completely flat, the actual surface area and geometric surface area would both be 1 cm$^2$. However if the flat surface was roughened by patterning, such as using photolithography and selective etching, the resulting actual surface area becomes much greater that the original geometric surface area due to the additional surface area provided by the sidewalls of the features generated. For example, if by roughening the exposed surface area becomes twice the surface area of the original flat surface, the R value would thus be 2.

The typography generally provides a roughness factor (R) of at least 2. It is believed that the effectiveness of a patterned coating according to the invention will improve with increasing pattern roughness above an R value of about 2, and then likely level off upon reaching some higher value of R. In a preferred embodiment, the roughness factor (R) is at least 4, such as 5, 6, 7, 8, 9, 10 11, 12, 13, 14, 15, 16, 17, 18, 19, 20, 25 or 30. Assuming deeper and more closely spaced features can be provided, R values can be higher than 30.

FIG. 1(a) is a scanned SEM image of an exemplary "Sharklet" topography according to an embodiment of the invention sized to resist algae adhesion and growth. The Sharklet topography is based on the topography of a shark's skin. Shark skin is a prominent example of a low friction surface in water. Unlike real shark skin which has fixed topographical feature dimensions based on the species, the Sharklet topography is scalable to any topographical feature dimension including feature width, feature height, feature geometry, and spacing between features. The composition of real shark skin is limited to the natural composition of the skin. The Sharklet topography according to the invention can be produced in a variety of material including synthetic polymers, ceramics, and metals, as well as composites.

In one embodiment, the groupings of features can have dilational symmetry. In another embodiment the groupings of features can have dilational symmetry in at least two different directions. In yet another embodiment, the groupings of features can have dilational symmetry in at least two mutually perpendicular directions.

Surface layer comprises a plurality of features 111 which are attached to and project out from base surface 130. Base surface 130 can be a roofing material, the inner surface of a water inlet pipe for a power or water treatment plant, an implantable medical device or material, such as a breast implant, a catheter or a heart valve. Each of the features 111 have at least one microscale dimension, with a width of about 3 μm, lengths of from about 3 to about 16 μm, and a feature spacing of about 1.5 μm. The thickness (height) of features 111 comprising coating layer is about three (3) microns.

Figure 8A:
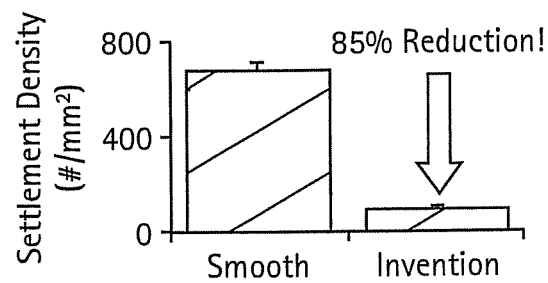
FIG. 8(a) shows settlement density data for algae spores on a smooth control sample as compared to the settlement density on the Sharklet surface architecture according to the invention shown in FIG. 1(a)
Figure 8B:
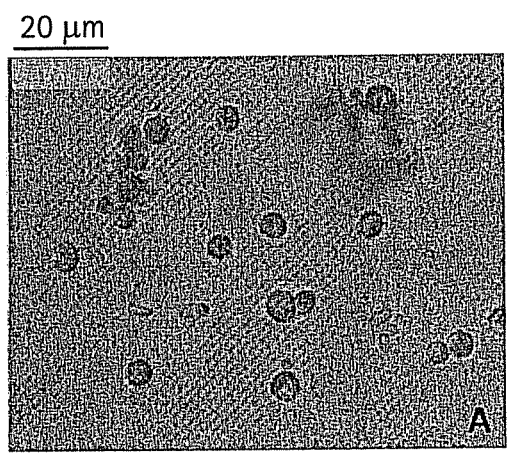
Figure 8C:
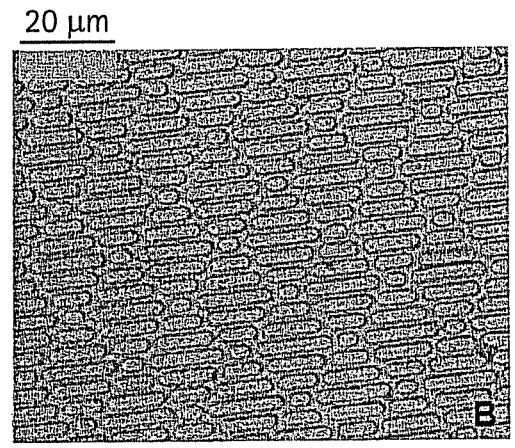
FIG. 8(c) is a scanned light micrograph image showing a dramatic reduction in algae spores on the surface of the surface architecture according to the invention shown in FIG. 1(a).

Features adjacent to a given feature 111 generally provide substantially different dimensions, in the arrangement shown in FIG. 1(a), feature lengths. The top surface of the features is shown as being planar. The patterned coating layer generally resists algae as compared to a generally planar base surface as described in the Examples and shown in FIGS. 8(a)-(c).

Figure 1B:
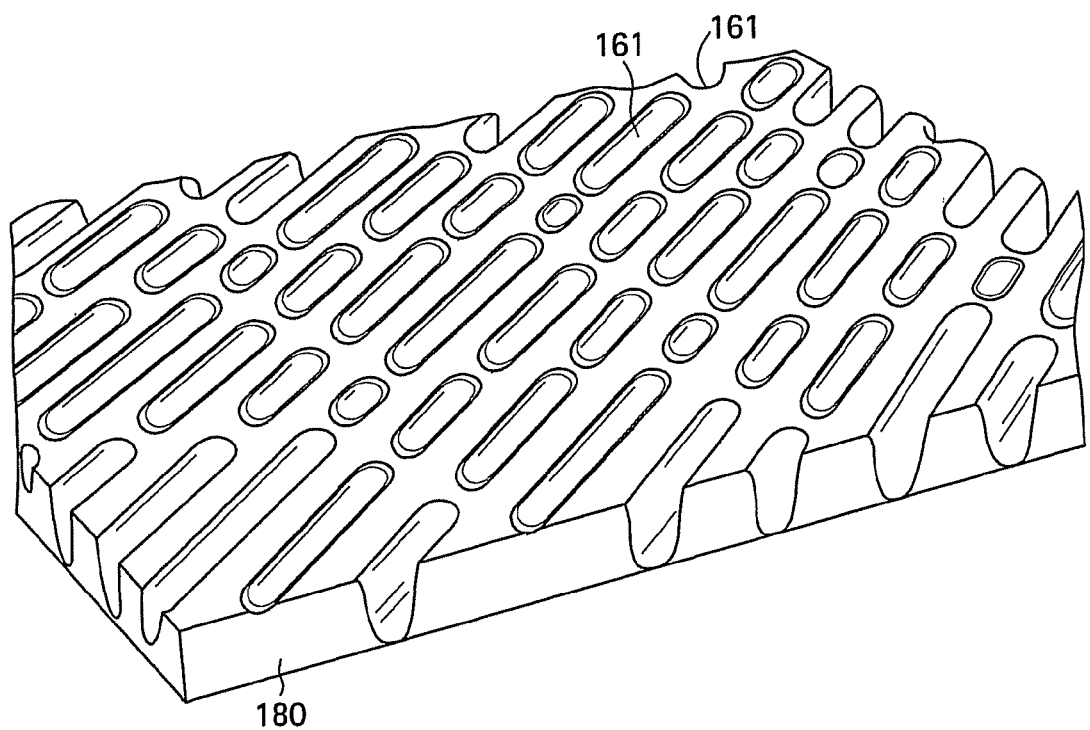
FIG. 1(b) is a scanned optical profilometry image of a pattern having a plurality of features projecting into the surface of a base article, according to another embodiment of the invention.

FIG. 1(b) is a scanned optical profilometry image of a pattern having a plurality of features 161 projecting into a base surface 180, according to another embodiment of the invention. Features 161 comprise indented void volumes into base surface 180. Although not shown, a surface can include regions having raised features 111 shown in FIG. 1(a) together with regions having indented features 161 shown in FIG. 1(b).

The composition of the patterned surface shown in FIGS. 1(a) and 1(b) is generally a polymer such as polymethylsiloxane (PDMS) elastomer SILASIC T2® provided by Dow Corning Corp, which is an elastomer of a relative low elastic modulus. The features 111 need not be formed from a single polymer. Features can be formed from copolymers and polymer composites. In another embodiment, the surface or coating comprises of a material such as, steel or aluminum, or a ceramic. The coating layer is also typically hydrophobic, but can also be neutral or hydrophilic.

As noted above, the patterned surface layer may also provide surface elastic properties which can influence the degree of bioadhesion directly, an in some cases, also modulate surface chemistry of the surface layer. It is believed that a low elastic modulus of the patterned coating layer tends to retard bioadhesion, while a high elastic modulus tends to promote bioadhesion. A low elastic modulus is generally from about 10 kPa and 10 MPa, while a high elastic modulus is generally at least 1 GPa.

The patterned surface can be formed or applied using a number of techniques, which generally depend on the area to be covered. For small area polymer layer applications, such as on the order of square millimeters, or less, techniques such as conventional photolithography, wet and dry etching, and ink jet printing can be used to form a desired polymer pattern. When larger area layers are required, such as on the order of square centimeters, or more, spray, dipcoat, hand paint or a variant of the well known "applique" method be used. These larger area techniques would effectively join a plurality of smaller regions configured as described above to provide a polymer pattern over a large area region, such as the region near and beneath the waterline of a ship.

A paper by Xia et al entitled "Soft Lithography" discloses a variety of techniques that may be suitable for forming comparatively large area surfaces according to the invention. Xia et al. is incorporated by reference into the present application. These techniques include micro contact printing, replica molding, microtransfer molding, micromolding in capillaries, and solvent-assisted micromolding, which can all generally be used to apply or form topographies according to the invention to surfaces. This surface topography according to the invention can thus be applied to devices as either a printed patterned, adhesive coating containing the topography, or applied directly to the surface of the device through micromolding.

Another tool that can be used is the Anvik HexScan® 1010 SDE microlithography system which is a commercially available system manufactured by Anvik Corporation, Hawthorne, N.Y. 10532. Such a tool could be used to produce surface topographies according to the invention over a large area very quickly. It has a 1 micron resolution which can produce our smallest pattern at a speed of approximately 90 panels (10" by 14") per hour.

Figure 2A:
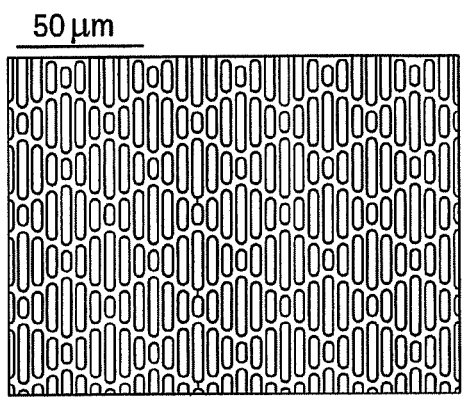
FIG. 2(a)-(d) illustrate some exemplary surface architectural patterns according to the invention.
Figure 2B:
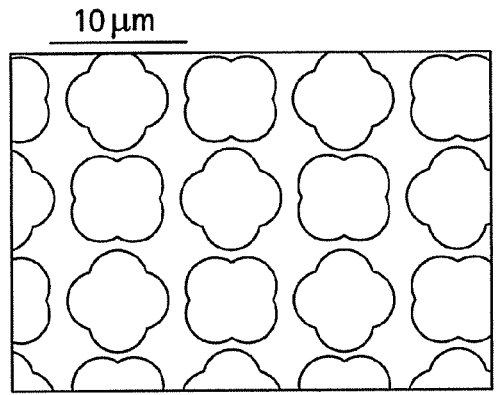
Figure 2C:
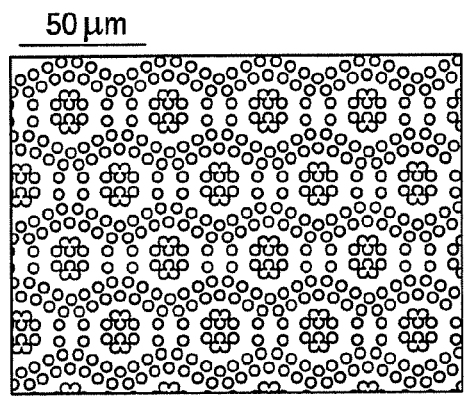
Figure 2D:
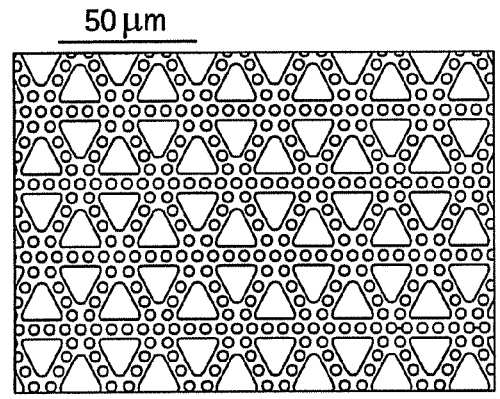

FIGS. 2(a)-(d) illustrate some exemplary architectural patterns (unit cells) that can be used with the invention. FIG. 2(a) shows a riblet pattern fabricated from PDMS elastomer having features spaced about 2 μm apart on a silicon wafer. The features were formed using conventional photolithographic processing. FIG. 2(b) shows a star/clover pattern, FIG. 2(c) a gradient pattern, while FIG. 2(d) shows a triangle/circle pattern.

FIG. 3 provides a table of exemplary feature depths, feature spacings, feature widths and the resulting roughness factor (R) based on the patterns shown in FIGS. 2(a)-(d). Regarding the riblet pattern shown in FIG. 2(a) for the depth, spacing and widths shown, the resulting pattern roughness factor (R) ranged from 5.0 to 8.9. Similar data for the star/clover pattern (FIG. 2(b)), gradient pattern (FIG. 2(c)), and triangle/circle (FIG. 2(d)) are also shown in FIG. 3. Regarding the triangle/circle arrangement (FIG. 2(d)), for a feature depth of 10 μm, feature spacing of 1 μm, and feature width of 1 μm (circles) and 5 μm (triangles), a roughness factor (R) of 13.9 is obtained.

Figure 4:
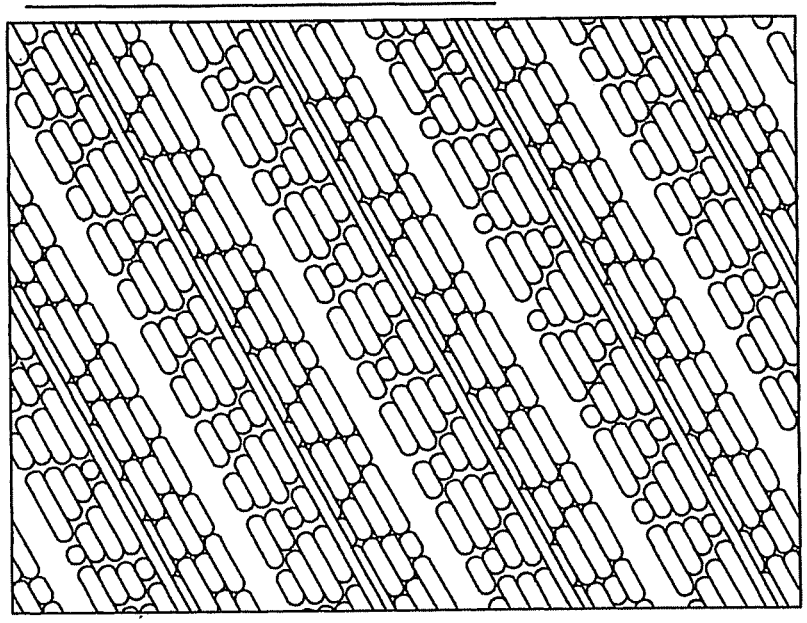
FIG. 4 is a depiction of an exemplary hierarchical surface topography according to an embodiment of the invention.

FIG. 4 is a scanned SEM image of an exemplary hierarchical (multi-layer) surface architecture according to an embodiment of the invention. The first feature spacing distance of about 2 μm between features 412 and its neighboring features including feature 411 is for deterring a first organism, or organism in a size range of about 5 μm, or less. For example, as noted above, an algae spore is nominally 5 μm wide. A patterned second layer comprising a plurality of striped plateau regions 420 is disposed on the first layer. A spacing distance between elements of the plateau layer provide a second feature spacing which is substantially different as compared to the first feature spacing. As used herein, a "substantially different spacing distance" is at least 50% larger, and is preferably at least 100% larger than the smaller first feature spacing distance. In FIG. 4, the architecture shown provides a spacing distance between the second pattern strips of about 20 μm, or about 900% greater than the first spacing distance. The 20 μm spacing is approximate ½ the width (smallest dimension) of a nominal barnacle thus repelling barnacles. Thus, hierarchical (multi-layer) surface architectures according to the invention can simultaneously repel multiple organisms covering a significant range of sizes.

In one embodiment of the invention, the surface topography is a topography that can be numerically represented using at least one sinusoidal function. In the paragraphs below, a sinusoidal description of Sharklet and related topographies is provided.

The Sharklet and related topographies can be numerically representing using two (2) sinusoidal waves. A general equation is provided which the only topographical restriction is that two elements with at least a one dimensional length discrepancy must be selected and periodic throughout the structure. The smallest feature of the two being related to the size of the smallest dimension (the width) of the organism of interest. All the elements and features in-between and/or around the two periodic features becomes irrelevant. Examples of each of these instances are presented and the generalized equation is then developed. In one embodiment, with reference to FIG. 1(a), it may be seen that the adjacent groupings of features are spaced apart from each other to define an intermediate sinusoidal pathway. It may further be seen by reference to FIG. 1(a) that neighboring sinusoidal paths converge toward and diverge from each other in a substantially mirror symmetry.

The Sharklet shown in FIG. 1(a) will be used for this example. The dimensions are not relevant as this point. The Sharklet shown in FIG. 1(a) is a 4-C element (repeating) structure.

Figure 5A:
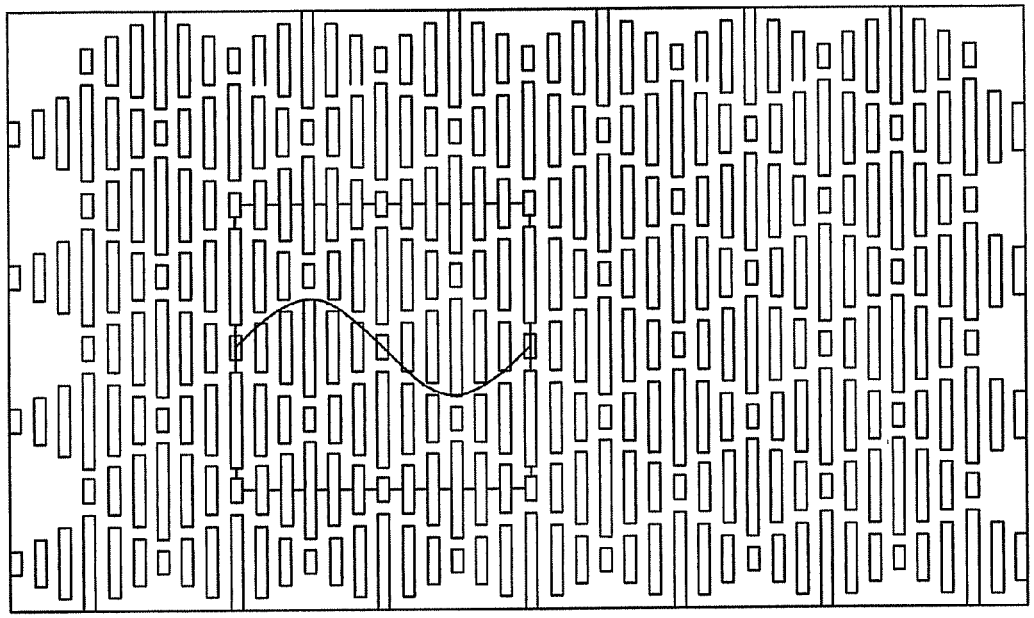
FIG. 5(a) shows a sinusoidal wave beginning at the centroid of the smallest (shortest) of the four features comprising the Sharklet pattern.
Figure 5B:
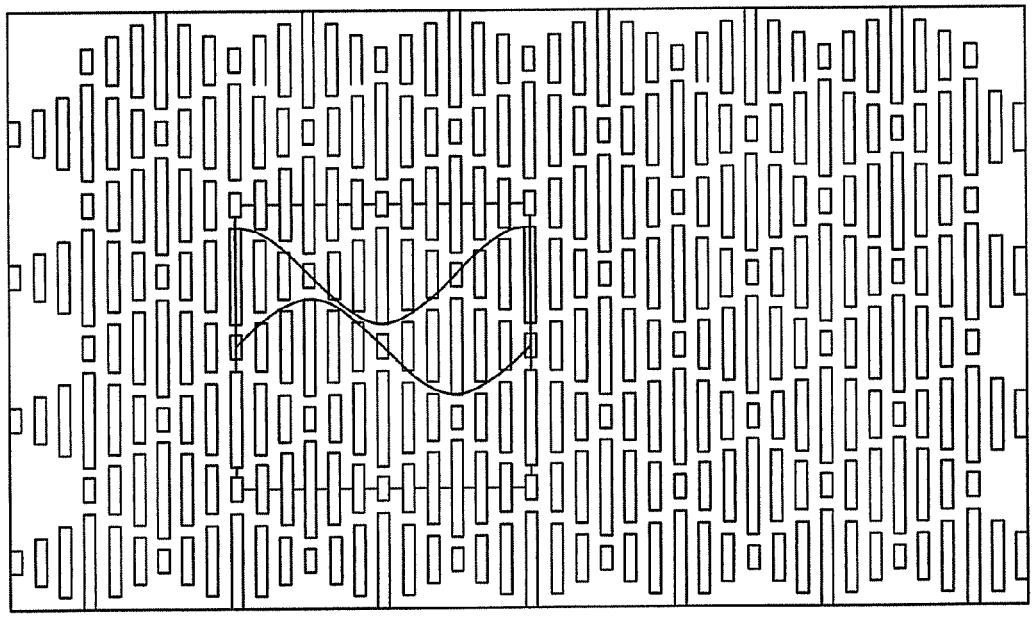
FIG. 5(b) shows sine and cosine waves describing the periodicity and packing of the Sharklet pattern.

FIG. 5(a) shows a sinusoidal wave beginning at the centroid of the smallest of the four Sharklet features. By inspection of the periodicity of the Sharklet features, a sine wave of the form y=A sin(wx) can be used to describe this periodicity as shown in FIG. 5(a). It can be noticed that the repeating structure above the section described by the sin wave is out of phase from that structure by 90 degrees or π/2 radians, which happens to be a cosine wave. That periodicity and packing can be represented using a cosine wave in the form y=B+A cosine (wx) (as shown in FIG. 5(b)).

The entire surface area of the topography can be numerically represented by a numerical summation of both sinusoidal waves in the form: y=cN+A sin(wx)y=cN+B+A cosine (wx) where N=0, 1, 2, 3 . . . n The area of coverage of the topography is thus described by the limits of n and x.

The Sharklet and related topographies can thus be defined by the following limitations:

Two geometric features of at least one dimensional discrepancy must be periodic throughout the structure.

The smallest of the two geometric features is related to the smallest dimension of the fouling organism or cell of interest.

In a standard Cartesian coordinate system represented by x and y, with the origin positioned at start of each sin and cosine wave, the smaller of the two features is periodic where the waves cross y=0. The waves pass through the area centroid of the feature @ y=0.

In a standard Cartesian coordinate system represented by x and y with the origin positioned at start of each sin and cosine wave, the larger of the two features is periodic where the waves cross reaches it's maximum amplitude. The wave intersects the center of the tallest part of the feature @ y=max and the x-moment of inertia of the feature @ y=0.

General Form of Sinusoids $$y=cN+A\sin(wx)$$

$$y=cN+B+A\cosine(wx) \text{ where } N=0, 1, 2, 3 \ldots n$$

The following equations define the values for the variables A,B,c and w:

$$A=(½)*(L_D)$$

$L_D$=y-dimension of larger of two elements B=(½)*($S_D$)+($P_S$)+(½)*($L_D$)

$S_D$ y-dimension of smaller of two elements $P_S$=y-spacing between the two elements after packing c=$L_D$+2*($P_S$)+$S_D$ w=2πf=(2π)/(T)→w: angular frequency (rad), f: frequency (Hz), T: wave period $$T=2*X_D$$

Figure 6A:
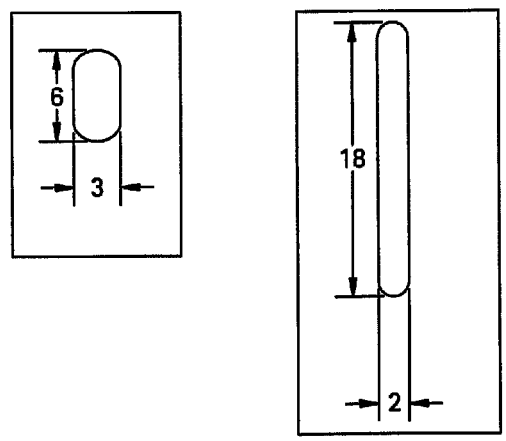
FIG. 6(a) shows two (of four) exemplary Sharklet elements, element 1 and element 2.
Figure 6B:
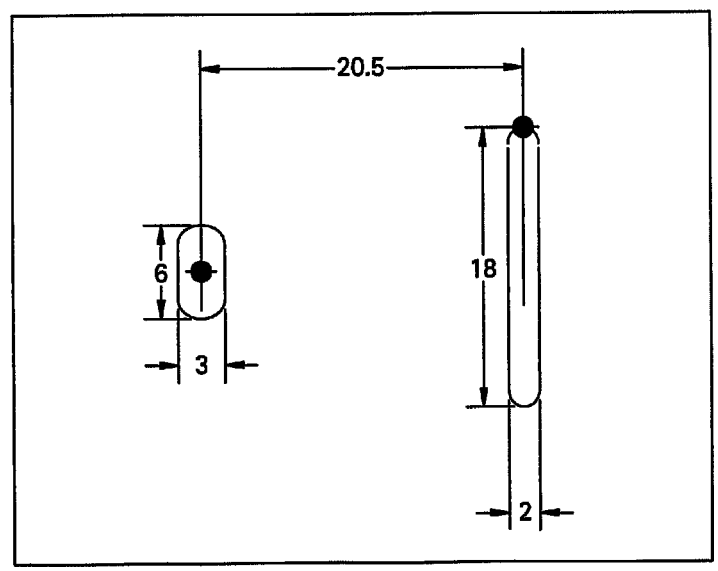
FIG. 6(b) shows the resulting layout after following limitations 3 & 4 (described below) and defining $X_D$. $P_S$ (y-spacing between smaller element and larger element after packing)

$X_D$=x-dimensions from centroid of smaller feature to the center of the tallest point on the larger feature Example Units=microns FIG. 6(a) shows element 1 and element 2. FIG. 6(b) shows the resulting layout after following limitations 3 & 4 and defining $X_D$. $P_S$ (y-spacing between smaller element and larger element after packing) are then set to 3 microns as shown in FIG. 6(c).

Variables are then calculated:

$$A=(½)*(18)=9$$

$$B=(½)*(6)+(3)+(½)*(18)=15$$

$$c=18+(2)*(3)+9=33$$

$$w=(2π)/(2*20.5)=π/20.5$$

Sinusoids are then defined.

$$y=33N+9\sin((π/20.5)x) \quad (1)$$

$$y=33N+15+9\cosine((π/20.5)x) \quad (2)$$

where N=0, 1, 2, 3 . . . n

Figure 7A:
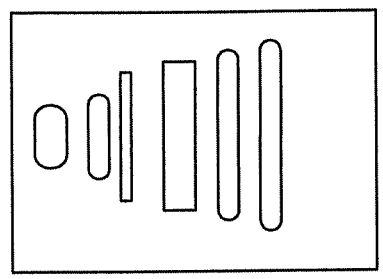
FIG. 7(a) shows a space filled with elements defined by limitations imposed.
Figure 7B:
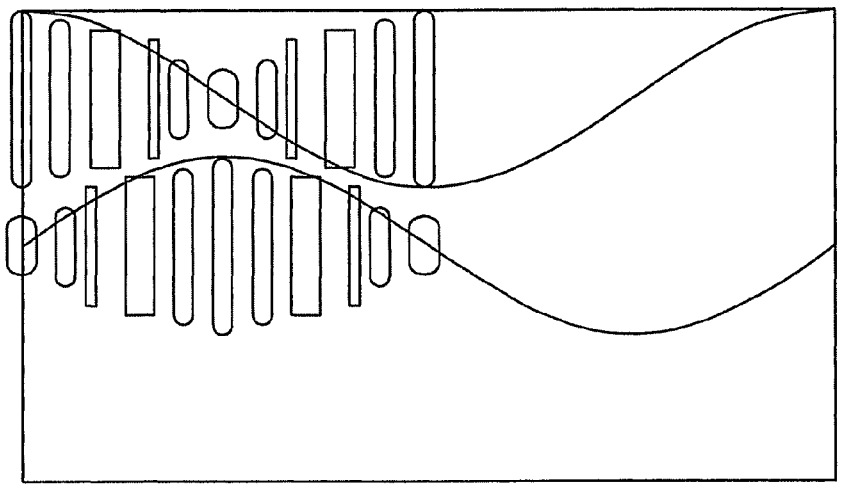
Figure 7C:
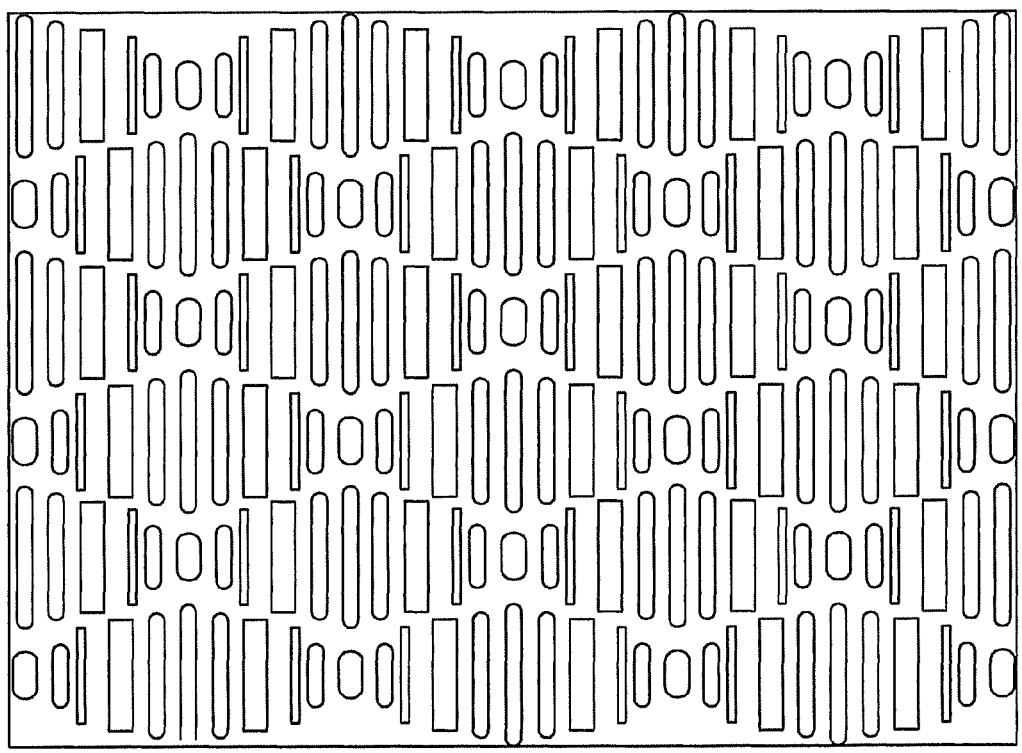
FIG. 7(c) shows the resulting topographical structure over the full area of the desired surface.

The space is then filled with elements between defined elements as shown in FIG. 7(a). Sinusoidal waves are then applied to define periodic repeat definitions as shown in FIG. 7(b) to create the desired topographical structure over the desired surface area shown in FIG. 7(c).

Another method for describing surface topographies according to the invention involves a newly devised engineered roughness index (ERI), first conceived of and used by the present Inventors. The ERI can characterize the roughness of an engineered surface topography. The ERI was developed to provide a more comprehensive quantitative description of engineered surface topography that expands on Wenzel's roughness factor (Wenzel R N. 1936, Resistance to solid surfaces to wetting by water. Ind Eng Chem 28:988-944). It has been found that Wenzel's description alone does not adequately capture the tortuosity of the engineered topographies studied. ERI is expressed as follows: ERI=$(r*df)/f_D$ (1) wherein the ERI encompasses three variables associated with the size, geometry, and spatial arrangement of the topographical features: Wenzel's roughness factor (r), depressed surface fraction ($f_D$), and degree of freedom for movement (df).

Wenzel's roughness factor refers to the ratio of the actual surface area to the projected planar surface area. The actual surface area includes areas associated with feature tops, feature walls, and depressed areas between features. The projected planar surface area includes just the feature tops and depressions.

The depressed surface fraction ($f_D$) is the ratio of the recessed surface area between protruded features and the projected planar surface area. This depressed surface fraction term is equivalent to both $1-\phi_S$ and $1-f_1$ where $\phi_S$ is the surface solid fraction as described by Quéré and colleagues (Bico J, Thiele U, Quéré D. 2002. Wetting of textured surfaces. Colloids Surf A: Physicochem Eng Aspects 206:41-46; Quéré D. 2002. Rough ideas on wetting. Physica A: Stat Theoret Phys 313:32-46) and $f_1$ is the solid-liquid interface term of the Cassie-Baxter relationship for wetting (Cassie A B D, Baxter S. 1944. Wettability of porous surfaces, Trans Faraday Soc 40:546-551).

The degree of freedom for movement relates to the tortuosity of the surface and refers to the ability of an organism (e.g. *Ulva* spore or barnacle) to follow recesses (i.e. grooves) between features within the topographical surface. If the recesses form a continuous and intersecting grid, movement in both the x and y coordinates is permitted and the degree of freedom is 2. Alternatively, if the grooves are individually isolated (e.g. as in channel topographies) then movement is only allowed in one coordinate direction and the degree of freedom is 1.

As such, as shown in FIG. 9 described in detail below, larger ERI values correlate with reduced settlement. In a preferred embodiment, the ERI is at least 5, and is preferably 8 or more.

A related surface description according to another embodiment of the invention comprises a polymer layer having a surface. The polymer layer is an elastomer containing a plurality of dissimilar neighboring protruding non-planar surface features where for repelling algae, the features are spaced between 0.5 and 5.0 microns. The features are such that the stress required to bend the feature is >10% greater than the stress required to strain a cell wall and where the features have a greater than 10% bending modulus difference in the bending modulus between two neighboring features, or in the case of three, or more neighboring features, their vector equivalence difference of >10%. Preferably, the surface features exist on the surface at a features per area concentration of >0.1 square microns.

The invention provides numerous benefits to a variety of applications since surface properties can be customized for specific applications. The invention can provide reduced energy and cost required to clean surfaces of biofouling by reducing biofouling in the first place. As a result, there can be longer times between maintenance/cleaning of surfaces. As explained below, the invention can also provide non-capsule formation due to foreign body response in the case of coated implanted articles. The invention can also be configured to provide enhanced adhesion to surfaces.

The present invention is thus expected to have broad application for a variety of products. Exemplary products that can benefit from the bioadhesion resistance provided by coating architectures according to the invention include, but are not limited to, the following:

a. biomedical implants, such as breast plant shells or other fluid filled implant shells;

b. biomedical instruments, such as heart valves;

c. Hospital surfaces, e.g., consider film (electrostatic) applications to surfaces that can be readily replaced between surgeries;

d. Clothing/protective personal wear;

e. Biomedical packaging;

f. Clean room surfaces, such as for the semiconductor or biomedical industry;

g. Food industry, including for packaging, food preparation surfaces;

h. Marine industry-including exterior surfaces of marine vessels including ships and associated bilge tanks and gray water tanks and water inlet/outlet pipes;

i. Water treatment plants including pumping stations;

j. Power plants;

k. Airline industry;

l. Furniture industry, such as for children's cribs;

m. Transportation industry, such as for ambulances, buses, public transit, and n. Swimming pools

EXAMPLES

It should be understood that the Examples described below are provided for illustrative purposes only and do not in any way define the scope of the invention.

An experiment was performed to compare the performance of an exemplary surface architecture according to the invention having features formed from a PDMS elastomer as compared to a planar uncoated control surface (the same PDMS elastomer) against bioadhesion of algae spores. The inventive surface topography was the Sharklet shown in FIG. 1(*a*). Following 45 minutes of exposure, as shown in FIG. 8(*a*), the settlement density of algae spores on the smooth control sample was about 720/mm$^2$, while the settlement density for the surface architecture according to the invention was only about 100/mm$^2$, or only about 15% of the settlement density of the control. FIG. 8(*b*) is a scanned light micrograph image of the surface of the control, while FIG. 8(*c*) is a scanned light micrograph image of the surface of the surface architecture according to the invention.

A further set of *Ulva* spore settlement assays were conducted to evaluate the impact of ERI. All pattern designs tested were transferred to photoresist-coated silicon wafers using previously described photolithographic techniques. Patterned silicon wafers were reactive ion etched, utilizing the Bosch process, to a depth of approximately 3 µm creating a topographical negative. Wafers were then stripped of photoresist and cleaned with an $O_2$ plasma etch. Hexamethyldisilazane was vapor deposited on the processed silicon wafers to methylate the surfaces in order to prevent adhesion.

Topographical surfaces were transferred to PDMSe from replication of the patterned silicon wafers. The resultant topographies contain features projecting from the surface at a height of approximately 3 µm. Pattern fidelity was evaluated with light and scanning electron microscopy.

*Ulva* spore settlement assays were conducted with 76 mm×25 mm glass microscope slides coated with smooth and topographically modified PDMSe surfaces. Glass slides coated with PDMSe topographies were fabricated using a two-step curing process as previously described (Carman et al. 2006). The resultant slide (~1 mm thickness) contained an adhered PDMSe film with a 25 mm×25 mm area containing topography bordered on both sides by 25 mm×25 mm smooth (no topography) areas.

Three replicates of each topographically-modified PDMSe sample, permanently adhered to glass microscope slides, were evaluated for settlement of *Ulva* spores. Topographies included the Sharklet (inset A; upper left), 2 µm diameter circular pillars (inset C; lower left), 2 µm wide ridges (inset D; lower right), and a multi-feature topography containing 10 µm equilateral triangles and 2 µm diameter circular pillars (inset B; upper right). A uniformly smooth PDMSe sample was included in the assay and served as a control for direct comparison.

Regarding the Sharklet, 2 µm ribs of various lengths were combined centered and in parallel at a feature spacing of 2 µm. The features were aligned in the following order as indicated by feature length (µm): 4, 8, 12, 16, 12, 8, and 4. This combination of features formed a diamond and was the repeat unit for the arrayed pattern. The spacing between each diamond unit was 2 µm. Similar to that of the skin of a shark in terms of feature arrangement, this pattern was designed such that no single feature is neighbored by a feature similar to itself.

Regarding the 2 µm diameter circular pillars shown in inset C, patterns of 2 µm pillars and 2 µm ridges were designed at an analogous feature spacing of 2 µm. The pillars were hexagonally packed so that the distance between any two pillars was 2 µm. Regarding the 2 µm wide ridges shown in inset D, the ridges were continuous in length and spaced by 2 µm channels (D).

Regarding the multi-feature pattern shown in inset B, the pattern was designed by combining 10 µm triangles and 2 µm pillars. Pillars were arranged in the same hexagonal packing order as in the uniform structure. At periodic intervals, a 10 µm equilateral triangle replaced a set of six 2 µm pillars forming the outline of a 10 µm triangle. Thus, this design maintained a 2 µm feature spacing between each edge of the triangle and pillars.

Fertile plants of *Ulva linza* were collected from Wembury beach, UK (latitude 50°18'N; 4°02'W). *Ulva* zoospores were released and prepared for attachment experiments as documented previously (Callow et al. 1997).

Topographical samples were pre-soaked in nanopure water for several days prior to the assay in order for the surfaces to fully wet. Samples were transferred to artificial seawater (TROPIC MARIN®) for 1 hour prior to experimentation without exposure to air. Samples were then rapidly transferred to assay dishes to minimize any dewetting of the topographical areas. Ten ml of spore suspension (adjusted to $2\times10^6$ ml$^{-1}$) were added to each dish and placed in darkness for 60 minutes. The slides were then rinsed and fixed with 2% glutaraldehyde in artificial seawater as described in Callow et al. (1997).

Spore counts were quantified using a Zeiss epifluorescence microscope attached to a Zeiss Kontron 3000 image analysis system (Callow et al. 2002). Thirty images and counts were obtained from each of three replicates at 1 mm intervals along both the vertical (15) and horizontal (15) axes of the slide.

Spore density was reported as the mean number of settled spores per mm$^2$ from 30 counts on each of three replicate slides±standard error (n=3). Statistical differences between surfaces were evaluated using a nested analysis of variance (ANOVA) followed the SNK (Student-Newman-Kuels) test for multiple comparisons. Replicate slides (3) of each surface (5) were treated as a nested variable within each surface.

The mean spore density measured for each of the studied PDMSe surfaces was plotted against the calculated engineered roughness index (ERI) to determine if any correlations existed. It must be noted that these ERI values are for a fixed feature spacing of 2 µm and depth of 3 µm.

Spores were calculated to settle at a mean density of 671±66 spores/mm$^2$ on the smooth PDMSe surface. All topographies showed a statistically significant reduction in spore density relative to this smooth surface as evaluated by ANOVA analysis followed by the SNK multiple comparison test. A lower mean spore density was measured on the triangles/pillars (279±66) compared to both the pillars (430±81) and ridges (460±54). The Sharklet topography had the lowest spore density (152±32) compared to all other surfaces.

For the 2 µm wide ridges, the majority of the settled spores were bridged between the top edges of neighboring ridges. A few smaller spores were found squeezed within the 2 µm wide channels between ridges.

Spores remained atop the hexagonal packed 2 µm diameter pillars. No settled spores were observed on flat areas between pillars. For the multi-feature topography containing both 10 µm triangles and 2 µm pillars, spores completely avoided settling on the flat top surface of the triangle. Most spores appeared to have settled on top of a pillar while leaning against the edge of the triangle feature. The table below provides the calculated ERI values for the studied topographical patterns.

TABLE

| | Feature Geometry | | | Engineered Roughness Index | | | |
|---|---|---|---|---|---|---|---|
| | depth | spacing | width | r | df | $f_D$ | ERI (r*df)/$f_D$ |
| | (µm) | | | | | | |
| Ridges | 3 | 2 | 2 | 2.5 | 1 | 0.50 | 5 |
| Pillars | 3 | 2 | 2 | 2.36 | 2 | 0.77 | 6.1 |
| Triangles/Pillars | 3 | 2 | 2, 10 | 2.23 | 2 | 0.51 | 8.7 |
| Sharklet | 3 | 2 | 2 | 2.5 | 2 | 0.53 | 9.5 |
| Smooth | n/a | n/a | n/a | 1 | 2 | 1 | 2 |

Calculated engineered roughness index (ERI) values for the studied topographical surfaces.

The mean spore density measured on each tested PDMSe surface was plotted against the calculated engineered roughness index (ERI) as shown in FIG. 9. A correlation was observed and a linear regression model was fit to the data. A fairly strong ($R^2$=0.69, p<0.001) inverse linear relationship existed between mean spore density and ERI by the following equation: Spore Density(spores/mm$^2$)=796−63.5*(ERI) (2)

The Sharklet had highest ERI (9.5) and lowest mean spore density. Following the trend, the triangles/pillars topography had the second highest ERI (8.7) and the second lowest mean spore density. Both the uniform ridges and pillars topographies had lower ERI values (5.0 and 6.1 respectively) and higher mean spore densities than both the Sharklet and triangles/pillars. There were no statistical differences in the mean spore densities of uniform ridges and pillars topographies.

Since feature width and spacing were the same for all these topographies, differences in ERI values were associated only with differences in feature geometry and tortuosity. This indicated that the geometric shape and arrangement of the individual features of Sharklet was likely critical because it enhanced anti-settlement effectiveness over topographies of equivalent dimensions.

Not all topographically modified or roughened surfaces have anti-settlement properties for *Ulva* spores. Spore settlement results on topographies presented here and previously have indicated that a critical interaction must be achieved between individual topographical features and the spore for the entire surface to be an effective inhibitory surface. Although trends with ERI values and spore settlement have been ascertained, it was only after topographic surfaces were designed at a feature spacing of 2 µm. This indicated that there exists an interaction between roughness measures and feature spacing that must be considered when designing topographic surfaces.

Figure 10:
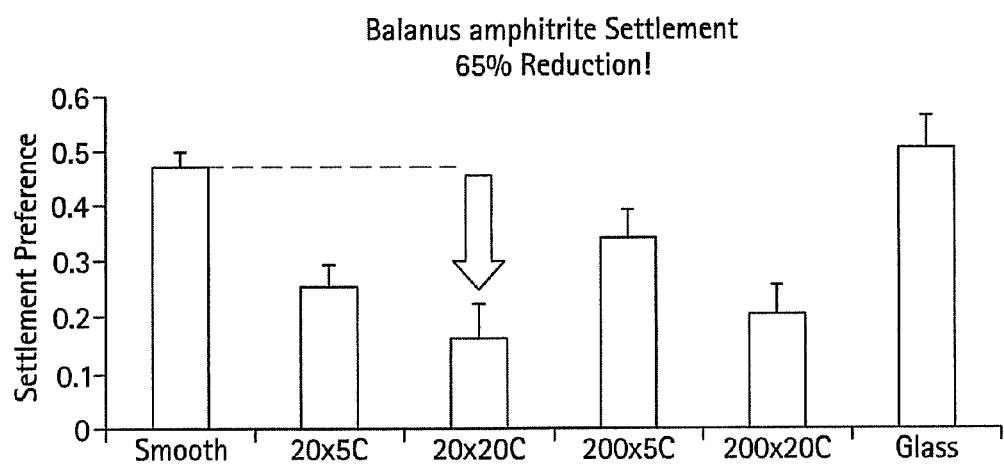
FIG. 10 shows settlement data from B. amphitrite on various (PDMS elastomer (PDMSe) channel topographies. Mean values±1 standard error are shown.

In another round of testing, sharklet surfaces according to the invention were prepared and tested for efficacy against barnacle adhesion. In the study, a surface comprising 20 µm×5 µm, 20 µm×20 µm, 200 µm×5 µm and 200 µm×20 µm PDMSe channels were evaluated for *B. amphitrite* (barnacle) settlement and release. The convention used herein is W×D, where W represents both the width and spacing between features and D represents the depth (height) of features. Although equal in this particular example, the invention is in no way limited to the width equaling the spacing. Incubation time was approximately 48 hours. All four topographies reduced settlement relative to a surface of smooth PDMSe. The most significant reduction in barnacle settlement of about 65% was provided by the 20×20 channels as shown in FIG. 10.

Based on the results of this study, surfaces were designed to probe the antifouling properties of topographical features with ~20 µm dimensions. Four replicates each of the following PDMSe topographies were prepared: smooth, 20×20 Channels (20CH), 20×40 Channels (40CH), 20×20 Sharklet (20SK) and 20×40 Sharklet (40SK). Four 0.5 cm$^3$ drops of artificial sea water (ASW) were deposited on each sample and then 10 cyprids dispersed in ~0.5 cm$^3$ ASW were added to each drop, bringing the total volume per drop to 1 cm$^3$. Samples were next placed in a humidified incubator at 28° C. for 24 hrs. Samples were inspected and settlement numbers (cyprids attached+cyprids metamorphosed) were counted. Samples were then returned to the incubator and read after subsequent 24 hr periods following the same protocol. The results collected at 24 and 48 hrs from the initial assay are referred to in the following sections as "assay 1".

Figure 11A:
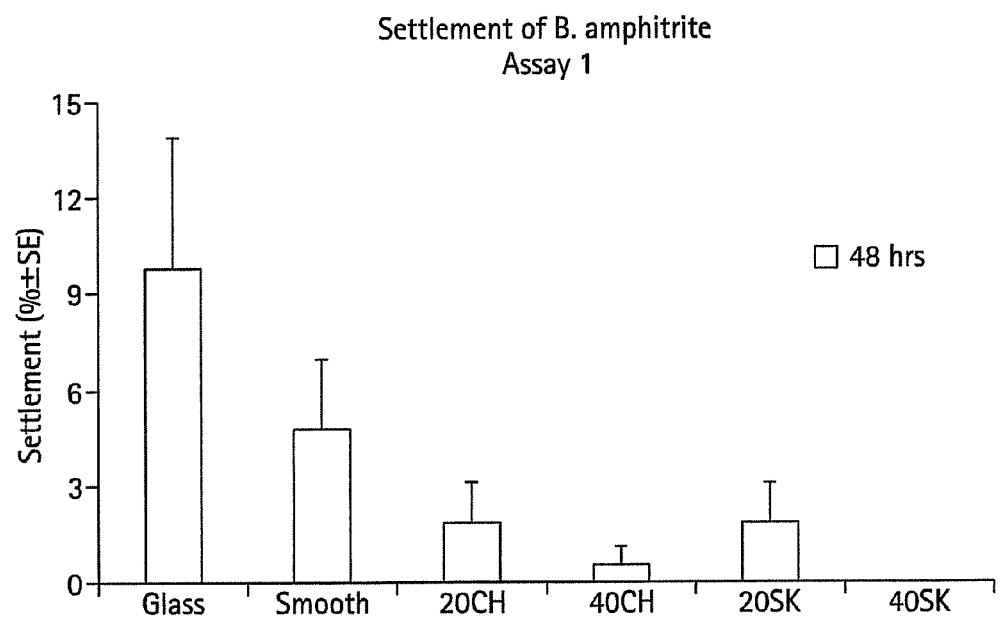
FIG. 11(a) is a chart showing barnacle cyprid settlement for a first assay (assay 1). Cyprids were allowed to settle for 48 hrs on each of the test surfaces. Topographies used included 20×20 channels (20CH), 20×20 Sharklet (20SK), 20×40 channels (40CH) and 20×40 Sharklet (40SK). Error bars represent ±1 standard error.
Figure 11B:
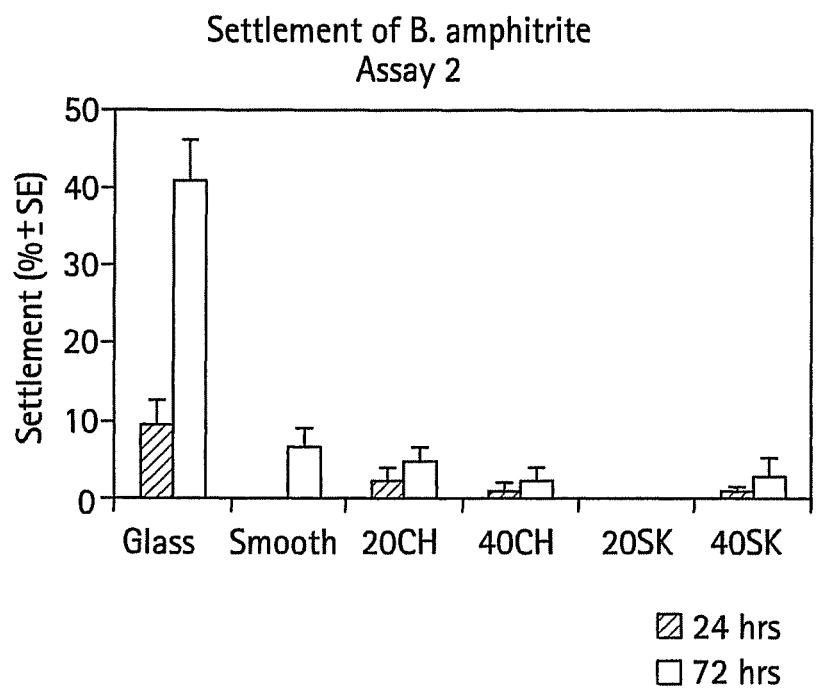
FIG. 11(b) is a chart of barnacle cyprid settlement for a second assay (assay 2). Cyprids were allowed to settle for up to 72 hrs on each of the test surfaces. Topographies used included 20×20 channels (20CH), 20×20 Sharklet (20SK), 40×40 channels (40CH) and 40×40 Sharklet (40SK). Error bars represent ±1 standard error.
Figure 11C:
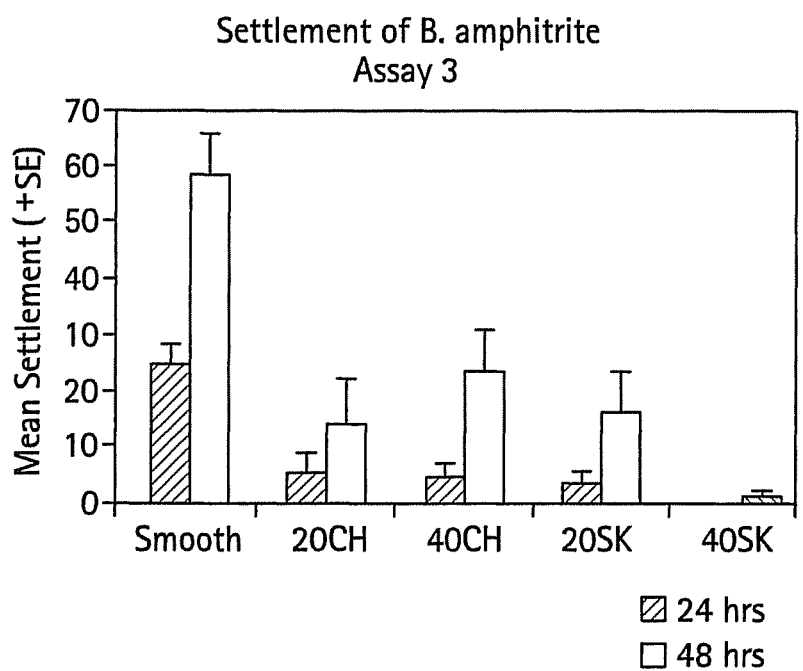
FIG. 11(c) is a chart of barnacle cyprid settlement for a third assay (assay 3). Cyprids were allowed to settle for up to 48 hrs on each of the test surfaces. Topographies used included 20×20 channels (20CH), 20×20 Sharklet (20SK), 40×40 channels (40CH) and 40×40 Sharklet (40SK). Error bars represent ±1 standard error.

In assay 1, settlement on all surfaces was negligible after 24 hrs, but the 48 hr results shown in FIG. 11(*a*) appear to indicate that all of the studied topographies reduce barnacle cyprid settlement. The 40SK topography completely inhibited barnacle settlement. However, because the overall settlement counts were quite low (~10% on glass), accurate statistical interpretation of the data was not possible.

Due to low overall cyprid settlement in assay 1, the decision was made to "clean" the test surfaces and repeat the process. Briefly, surfaces were rinsed in an excess of nanopure water, gently agitated in 90% ethanol on an orbital shaker over night, and subsequently rinsed in nanopure water and allowed to dry in air. On all PDMSe surfaces there was still a vague droplet outline evident following this procedure. Closer inspection suggested that this deposit may be bacterial biofilm. Assay 2 droplets were deposited on areas of the samples not previously used for assay. The results of this second round of testing will be referred to as "assay 2" in which readings were taken after 24 and 72 hrs. Cyprids were allowed to explore for longer in assay 2 to increase settlement, but the 48 hr reading was removed to prevent the potential loss of test droplets during transfer to and from the incubator. After the 24 hr reading, salinity in most of the test droplets had increased through evaporation from ~33 ppt to ~40 ppt so reverse osmosis (RO) water was added to each droplet to return the salinity back to ~33 ppt. For assay 2, significant results were found between glass and all PDMSe surfaces as shown in FIG. 11(*b*) after both 24 and 72 hrs. The 20SK topography completely inhibited barnacle settlement. However, there were still no significant differences detected between the smooth PDMSe control and the textured inventive surfaces. A repeat experiment with a fresh cyprid batch and new test surfaces was sought so that a definitive conclusion could be reached.

After the completion of assay 2, fresh samples were used to replicate the study. Using the same protocol as before, settlement was evaluated at 24 and 48 hrs for this study (assay 3). All topographies yielded significantly lower settlement compared to smooth after 24 hrs as shown in FIG. 11(*c*). After 48 hrs, the 20CH and 40SK topographies both showed a significant inhibitory affect on settlement. The 40SK topography almost completely inhibited settlement of the cyprids, which is consistent with assay 1 results. No significant differences were detected between the various topographies according to the invention.

Additional tests were performed to evaluate critical surface dimensions for bacteria. Recent literature on the relationship between zoospores and bacteria cells suggest that zoospores of eukaryote alga can sense a chemical signal produced by bacteria by utilizing a bacterial sensory system. As such, bacterial bio films have a direct influence on the development of algal communities. Work by the present Inventors with barnacle cyprids as discussed above has also shown the presence of something resembling a bacterial biofilm that was found to remain after washing. These findings suggest that disrupting the bacterial colonization of surfaces can in turn disrupt the settlement of larger organisms such as zoospores or cyprids.

In the investigation with the bacteria *Staphylococcus aureus*, Sharklet topography with 2 µm spacing dimensions was chosen to accommodate isolated, individual bacterium (cell size ~1-2 µm) to prohibit connectivity between bacteria cells thus prohibiting the formation of a confluent biofilm. Samples of 2 µm Sharklet PDMSe, smooth PDMSe, and glass were statically exposed to $10^7$ CFU/mL in growth medium for up to 12 days to promote biofilm formation. Samples were removed on the $2^{nd}$, $4^{th}$, $7^{th}$, and $12^{th}$ days, gently rinsed by immersion in de-ionized water, and air-dried for characterization.

After 12 days, scanning electron micrographs (SEM) revealed abundant biofilm on glass and slightly less on the smooth PDMSe, but no evidence of biofilm on the Sharklet surface. The SEM images acquired also suggest inhibition of bacterial cell settlement on the Sharklet surface.

It is to be understood that while the invention has been described in conjunction with the preferred specific embodiments thereof, that the foregoing description as well as the examples, which follow are intended to illustrate and not limit the scope of the invention. Other aspects, advantages and modifications within the scope of the invention will be apparent to those skilled in the art to which the invention pertains.

What is claimed is:

1. An article having a surface topography for resisting bio adhesion of organisms, comprising:
 a base article having a surface;
 a plurality of spaced apart features projected into said base surface, wherein each feature has a substantially different geometry than neighboring features, wherein neighboring patterns share a common feature;
 the plurality of spaced features arranged in a plurality of groupings wherein each grouping is identical with other groupings; wherein each grouping has at least three features having a substantially different geometry from each other; and the spaced features within each of the groupings being spaced apart at an average distance of about 0.5 micrometers to about 200 micrometers; the adjacent groupings of features being spaced from each other to define an intermediate sinusoidal pathway, wherein neighboring sinusoidal paths converge toward and diverge from each other in a substantially mirror symmetry; further wherein a width of each sinusoidal path as measured between two adjacent groupings is substantially uniform.

2. The article of claim 1, wherein the sinusoidal path has at least two or more directions.

3. The article of claim 1, wherein the plurality of spaced features has a similar chemical composition to the surface.

4. The article of claim 1, wherein the plurality of spaced features has a different chemical composition from that of the surface.

5. The article of claim 1, wherein the plurality of spaced features is applied to the surface in the form of a coating.

6. The article of claim 1, wherein the plurality of spaced features comprises an organic polymer, a ceramic or a metal.

7. The article of claim 1, wherein the groupings of features are arranged with respect to one another so as to define a linear path or a plurality of channels.

8. The article of claim 1, wherein the sinusoidal path is defined by a sinusoidal function.

9. The article of claim 1, wherein one or more features are shared between groupings.

10. The article of claim 1, wherein the groupings have patterns of features.

11. The article of claim 1, wherein the features are periodic.

12. The article of claim 1, wherein the features are aperiodic.

13. The article of claim 1, wherein the features have a roughness factor (R) of about 2 to about 30.

14. The article of claim 1, wherein the plurality of spaced features have a first spacing and have disposed thereon a second plurality of spaced features having a second spacing.

15. The article of claim 1, wherein each grouping comprises at least four features that have a substantially different geometry from each another.

16. The article of claim 1, wherein each grouping comprises at least five features that have a substantially different geometry from each another.

17. The article of claim 1, wherein each grouping comprises at least six features that have a substantially different geometry from each another.

* * * * *